(12) United States Patent
Ward et al.

(10) Patent No.: US 7,045,655 B2
(45) Date of Patent: *May 16, 2006

(54) PREPARATION AND PURIFICATION OF HYDROXYLAMINE STABILIZERS

(75) Inventors: Irl E. Ward, Bethlehem, PA (US); Danielle French, West Warren, MA (US)

(73) Assignee: BASF Aktiengesellschaft, Ludwigshafen (DE)

( * ) Notice: Subject to any disclaimer, the term of this patent is extended or adjusted under 35 U.S.C. 154(b) by 92 days.

This patent is subject to a terminal disclaimer.

(21) Appl. No.: 10/731,123

(22) Filed: Dec. 10, 2003

(65) Prior Publication Data

US 2005/0131250 A1    Jun. 16, 2005

(51) Int. Cl.
*C07C 229/00* (2006.01)

(52) U.S. Cl. .................................................... 562/507

(58) Field of Classification Search ............... None
See application file for complete search history.

(56) References Cited

U.S. PATENT DOCUMENTS

| 2,519,708 | A | * | 8/1950 | Schlapfer et al. ........... 562/507 |
| 4,166,842 | A |   | 9/1979 | Tunick et al. |
| 5,808,150 | A |   | 9/1998 | Michelotti |

* cited by examiner

*Primary Examiner*—Paul A. Zucker
(74) *Attorney, Agent, or Firm*—Novak Druce & Quigg, LLP; Jason B. Voight

(57) ABSTRACT

The invention relates to the preparation of ultra-high purity 1,2-diaminocyclohexane-tetraacetic acid being essentially free of unwanted metal and metal ion contaminants and its use as a stabilizer for ultra-high purity hydroxylamine compounds used extensively in the production of high premium electronic components.

13 Claims, No Drawings

PREPARATION AND PURIFICATION OF HYDROXYLAMINE STABILIZERS

FIELD OF THE INVENTION

The present invention relates to a process for the preparation of ultrapure 1,2-diaminocycloalkyl-N,N,N',N'-tetraacetic acid (CDTA) compounds and their use as stabilizers for hydroxylamine compositions.

DESCRIPTION OF THE PRIOR ART

Hydroxylamine compounds are important chemical intermediates in various processes, especially in the microelectronic, pharmaceutical and agricultural industries. In the microelectronic industry hydroxylamine compounds are used in printed circuit board fabrication, in microelectronic chip manufacture and in similar technology. For example, hydroxylamine compositions are extensively utilized as components of so-called "stripper" solutions for removing developed photoresists such as polyimide coatings from metal foils. In the pharmaceutical industry and in agricultural chemicals, the compounds are used as an intermediate in various chemical syntheses for commercially available products.

Utilization of hydroxylamine solutions for most of these purposes requires an ultra-high purity form of the material. A major concern at every stage in the manufacture of electronic components is contamination. Control of contamination is critical to product quality. These requirements are particularly acute in the manufacture of very high density circuitry and in ultra-high precision manufacturing. Frequently, solutions of hydroxylamine contain undesirable amounts of anion and cation impurities particularly of various metal and metal ion contaminations. In hydroxylamine photoresist stripper solutions such impurities even in trace amounts when introduced onto a semiconductor chip during its manufacture, tend to produce localized defects in the crystalline structure which may then propagate to produce undesirable pittings and render the chip deficient or even useless for its intended purpose.

Often it is necessary to employ hydroxylamine in the form of a solution of free base which is generally liberated from a hydroxylamine salt such as hydroxylamine chloride or hydroxylamine sulfate by the action of an appropriate base such as ammonia, alkali metal hydroxides or an alcoholate. Neutral or alkaline hydroxylamine solutions are unstable and decompose exothermically by internal oxidation-reduction reaction to form ammonia, nitrogen, oxides of nitrogen and water.

The rate of decomposition is accelerated by a high pH and a high concentration of catalytically active impurities. In order to avoid decomposition of the hydroxylamine, a stabilizer is added to the solution. Numerous stabilizers for hydroxylamines are already known. However, few stabilizers proposed to date have been of ultra high purity so as not to contaminate either the hydroxylamine solution per se or the ion exchange resins used to purify the solution.

U.S. Pat. No. 4,166,842 to Tunick et al., which is incorporated herein by reference, discloses the purification of hydroxylamine by liquid/liquid extraction.

U.S. Pat. No. 5,808,150 issued to Michelotti which is incorporated herein by reference, discloses stabilizing aqueous, semi-aqueous or non-aqueous solutions containing hydroxylamine or a partially neutralized hydroxylamine salt utilizing 1,2-diaminocyclohexane-N,N,N',N'-tetraacetic acid ("CDTA") to minimize the decomposition and provide stability over a longer period than known stabilizers such as nitrilotriacetic acid and ethylene diamine tetraacetic acid. However, as commercially supplied for production purposes, CDTA contains a considerable amount of undesirable metals and metal ions, which even at the low stabilizing amounts (i.e. 100 parts per million) imports an increase in the treated hydroxylamine solution of the undesirable materials as to exceed the allowable limit of 10 parts per billion required for an ultrahigh pure grade hydroxylamine compound solution.

Clearly there is a need for an economical and relatively simple process to produce an ultrahigh purity CDTA particularly for use as a stabilizer for hydroxylamine compound solutions, which will provide a high yield of acceptable product for use in a wide variety of applications, especially those requiring high purity aqueous solutions of hydroxylamine.

This need is met by a process for preparing cis-or trans-1,2-diaminocyclohexane-N,N,N',N'-tetraacetic acid which comprises the steps of (a) neutralizing an aqueous solution of chloroacetic acid with a nonmetal amino or hydroxide base;

(b) reacting cis- or trans-1,2-diaminocyclohexane with the neutralized chloroacetic acid of step (a) at an elevated temperature;

(c) treating the product from step (b) with a non-metal amino or hydroxide base;

(d) treating the resulting product of step (c) with acid and then (e) recovering the product formed.

DETAILED DESCRIPTION OF THE PREFERRED EMBODIMENTS

The synthesis of cis- or trans-1,2-diamino-cyclo-hexane-N,N,N',N'-tetraacetic acid is a multi stage process carried out in an aqueous medium, at least using deionized water but preferably distilled water. The initial step involves a neutralization reaction involving chloroacetic acid and a non-metal amine or hydroxide base solution. The chloroacetic acid is dissolved in water in a concentration of about 20–70 weight percent and preferably about 30 weight percent and the temperature is lowered to 0° C. About one-half of the neutralizing agent is added at this temperature in the form of a 10 weight percent solution of the non-metal amino or hydroxide base solution to begin forming a chloroacetic acid-nonmetal ionic complex maintaining the temperature below 10° C. Cis- or trans-1,2-diaminocyclohexane is added and the reaction mixture is heated slowly. Using cis- or trans-1,2-diaminocyclohexane determines wether cis- or trans-CDTA will be produced. The stereoisomerism remains unchanged. When the temperature reaches about 20° C. the other half portion of the neutralizing agent is added dropwise while the heating continues slowly to about 75° C.–80° C. Upon completion of the addition of the neutralizing agent, the reaction is stirred and heated up to about, but not to exceed 100° C. for one hour. After the reaction is complete, the mixture is cooled and filtered for example using an aspirator filter to separate any formed crystals. The filtrate is slowly acidified with concentrated hydrochloric acid. At about pH 3 a precipitate will begin to form as crystals in the filtrate. The filtrate is then stirred, typically for 5 to 10 minutes. After the stirring period more hydrochloric acid is added dropwise until pH 2 is reached. The stirring is continued, typically for another 5 to 10 minutes, and the filtrate is filtered and the CDTA crystals are recovered. Constant stirring and slow addition of the hydrochloric acid are critical to provide a maximum yield. The final step in the synthesis involves a recrystallization in which a small portion of the CDTA prepared, as described above, are dissolved in deionized water and sufficient amount of non-metal base solution is added until the crystals are dissolved in the solution (at about pH 6–7). Dilute hydrochloric acid is added dropwise slowly until the CDTA precipitated (about pH 4). The filtrate was also treated with diluted hydrochloric acid and a precipitate formed (about pH 2). All the precipitates may be collected for further processing.

The synthesis of 1,2-diaminocyclohexane-N,N,N',N'-tetraacetic acid according to the present invention is a multi-stage process carried out in an aqueous medium and the following equations show the reactions in the various stages, with TMAOH being used as an example of a base in the first step and 30% NH$_4$OH being used as an example of a base in the second step:

first step (step(1))

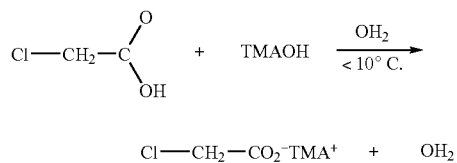

$$Cl-CH_2-CO_2^-TMA^+ \quad + \quad OH_2$$

second step (step(2))

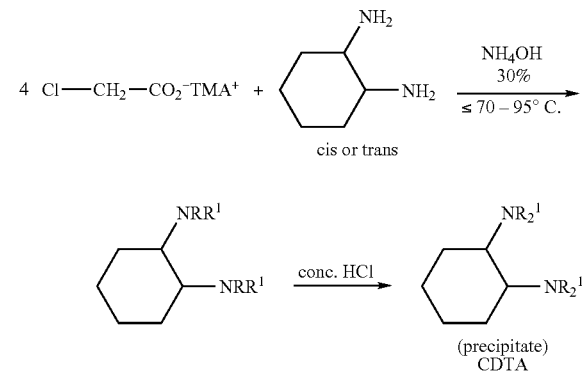

(precipitate)
CDTA

TMA: trimethylammonium
TMAOH=trimethylammonium hydroxide
Wherein R is CH$_2$COOTMA and R$^1$ is CH$_2$COOH A recrystallization process follows the above synthesis schemes to remove substantially any traces of the unwanted metals and metal ions. As described above, the process involves dissolving the CDTA in deionized water adding a non-metallic amino or hydroxide base to a pH of 6–7, and precipitating the CDTA by the slow addition of diluted hydrochloric acid to pH 4. After the precipitate forms the slow addition of diluted hydrochloric acid may continue until a pH 2 is reached. The CDTA produced is of an ultra-high purity grade.

Non-metal amino or hydroxide bases are used for dissolving the free acid form of CDTA for the synthesis or for the recrystallization step. For the synthesis procedure the non-metal amino or hydroxide bases must be used in step (1) and (2). They need not be the same caustic. For example, trimethylammonium hydroxide is used in step (1) and ammonium hydroxide in step (2).

Suitable non-metal amino or hydroxide bases useful in the CDTA synthesis are represented by the following formulae:

NH$_4$OH

R$_X$NH$_Y$$^+$OH$^-$ where: R=alkyl; x=1–4; y=0–3; x+y=4

R$_X$NH$_Y$ where: R=alkyl or alkanol; x=1–3; y=0–2; x+y=3

(NH$_4$)$_X$H$_Y$PO$_4$ where: x=1–3; y=0–2; x+y=3

(R$_X$NH$_Y$) acetate where: R=alkyl; x=0–4; y=0–4; x=y=4

Examples of suitable bases are sodium hydroxide, tetraalkyl ammonium hydroxide solutions, eg. tetramethyl ammonium hydroxide solution, tetraethylammonium hydroxide, alkanolamines such as monoethanolamine, isopropylamines, diethanolamine, 2-amino-1-propanol; 2-amino-2-ethoxypropanol, ammonium hydroxide, inter alia. When using ammonium hydroxide the solutions should be freshly made and used preferably within 6 hours, since after about six hours storage the solution starts to lose concentration, and at 24 hours deterioration becomes extensive.

Typically as an article of commerce CDTA as supplied contains 1000–5000 ppm of unwanted metal or metal ions. Thus, by adding a conventional amount of stabilizer about 100 ppm to the hydroxylamine solution the unwanted metal or metal ions would range from 100 to 500 ppb. This is clearly unacceptable for the stabilization of ultra-high purity grade hydroxylamine solutions, typically electronics grade where all the undesirable metals must be no more than 10 ppb.

The metals which play havoc in the production of high precision electronic components include alkali, alkaline earth metals and transition metals and ions thereof. Specific examples of commonly encountered unwanted metals and the corresponding ions include aluminium, calcium, chromium, cobalt, copper, iron, magnesium, potassium, and sodium.

The amount of stabilizer to be used to stabilize the hydroxylamine or the at least partially neutralized hydroxylamine salt solution ranges from about 0.001 to about 0.1 percent by weight of composition. Preferably, the amount of stabilizer ranges from about 0.01 to about 0.5 percent (100 to 500 ppm) same basis. The aqueous solutions of free hydroxylamine, i.e., fully neutralized salt, can be produced by the reaction of a salt of hydroxylamine (such as the hydrochloride, the nitrate, the acetate, the sulfate, etc.) with an alkali metal hydroxide (such as sodium hydroxide) or with ammonia. The concentration of the hydroxylamine salt is usually at least about 1 weight percent of the aqueous solution and can range up to about 70 percent or more, but is generally in the range form about 10 to 70 weight percent. It is best to add the stabilizer to the hydroxylamine salt solution before its neutralization with a base, but the stabilizer can also be added to the at least partially neutralized hydroxylamine salt solution and salt-free hydroxylamine solutions. The temperature during the addition being advantageously kept at from 5 degree(s) to about 40 degree(s) Celsius. The stabilized solutions should be stored at temperature <40 degree(s) Celsius, preferably <25 degree(s) Celsius.

It has been surprisingly found that the stabilizers of the invention also provide a caging effect similar in concept and practice to crown ethers. This is due to the chemical and physical nature of the stabilizers of the present invention. When used in small amounts, the stabilizer acts as a host molecule and assumes a shape required for the formation of a complex or adduct to form a "cage" around and alkali or multivalent alkali metal ion. This action prevents any redeposition of or multivalent alkali metal ions onto a metal or non-metal wafer substrate during stripping when used in a stripping composition. For this purpose, the stabilizers of the present invention can be used in stripper formulations independent of hydroxylamine.

Hydroxylamine compounds can be stabilized by the ultra-high purity CDTA of the present invention include solutions of hydroxylamine or at least partially neutralized hydroxylamine salt and organic hydroxylamines. Hydroxylamine compounds may be represented by the formula:

$$NR_3R_2OH$$

wherein $R_3$ and $R_2$ are independently hydrogen or hydrocarbyl groups containing 1 to about 6 carbon atoms, and preferably $R_3$ and $R_2$ are independently hydrogen or hydrocarbyl groups containing 1 to about 3 carbon atoms.

Specific examples of $R_2$ an $R_3$ include hydrogen, and alkyl groups such as methyl, ethyl, propyl, including isopropyl, butyl, etc. In embodiments where $R_2$ and $R_3$ are hydrogen, the hydroxylamine compound is hydroxylamine. In embodiment where at least one $R_2$ and $R_3$ is hydrocarbyl group, the hydroxylamine compound is an organic hydroxylamine. The term "hydrocarbyl" is used herein to include hydrocarbyl as well as substantially hydrocarbyl which means that non-hydrocarbyl substituents do not effect the hydrocarbyl substituents characteristics or properties. Examples of organic hydroxylamines include methylhydroxylamine, isopropylhydroxylamine and diethylhydroxylamine.

The following examples are set forth for purposes of illustration only and are not to be construed as limitations on the present invention except as set forth in the appended claims. All parts and percentages are by weight unless otherwise specified.

EXAMPLE 1

Into a vessel equipped with parts to accommodate a thermometer, a condensing column with a reflex cap, and a graduated liquid dropping column with a stopcock were charged 85 g of chloroacetic acid and dissolved in 200 g of deionized (DI) water. The solution was cooled to 0° C. and 135 g of 10% aqueous solution of Tetramethylammonium hydroxide were added to neutralize the acid. During the neutralization the temperature did not exceed 10° C. 26 g of 1,2-diaminocyclohexane were added and the reaction mixture was stirred for 1 hour at 100° C. and then cooled to room temperature. The product was acidified slowly with 100 g of concentrated hydrochloric acid to pH 3 with cloudy solution formation. The cloudy solution was stirred for about 5 to 10 minutes. Additional concentrated hydrochloric acid was slowly added dropwise until a pH 2 was reached and a precipitate was formed. The product was filtered and 1,2-diaminocyclohexane tetraacetic acid crystals were recovered.

A portion (39.9 g) of the CDTA crystals was dissolved in another vessel in 100 ml, of DI water to which was added while stirring constantly 30% aqueous ammonium hydroxide (freshly made) until all the CDTA crystals dissolved to form a clear solution at a pH 6 to 10. A diluted 18.5% hydrochloric acid was added slowly dropwise until a pH 4 was reached where the CDTA begins to recrystallize into a cloudy solution. The mixture was stirred for about 5 to 10 minutes. Again diluted to 5% hydrochloric acid was added slowly dropwise until a pH 2 was reached an complete crystallization occurs. The mixture was filtered and the CDTA recovered.

The use of an ion exchange process for purifying hydroxylamine is well know. The following example shows the use of the CDTA of the present invention to stabilize an ultra-high purity grade hydroxylamine purified by an ion exchange method.

EXAMPLE 2

Into a 1 inch diameter glass column containing a stopcock was added 25 ml of Purolite CT-151 cation exchange resin. The column was flushed with 1 liter of DI water. The resin was then flushed with 1000 ml of 10% hydrochlorid acid. The column was tested by inductively coupled plasma (ICP) analysis to determine if all undesirable cations are removed. The column was then flushed with DI water until the chloride ion level was <0.5 ppm.

A 5% hydroxylamine solution was poured through the column to convert the acid groups to the amino salt and there was a mild exothermic reaction. After the isotherm was complete, a 50% hydroxylamine solution was passed through the column.

A glass column was prepared with Purolite anion exchange resin A-400 similar to Part. I. 1000 ml of 8% KOH were passed through the column and the column was then flushed with 2 liters of DI water until the K+ analysis by ICP was <5 ppb. The 50% hydroxylamine solution processed was then passed through the anion exchange resin. The resulting solution was stabilized with 0.5% by weight of 1,2-diaminocyclohexane-N,N,N',N'-tetraacetic acid. The resulting solution could be used in the preparation of a photoresist stripping composition having a metal and metal ion content of less than 10 ppb.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A process for preparing cis- or trans-1,2-diaminocyclohexane-N,N,N',N'-tetraacetic acid which comprises the steps of
   (a) neutralizing an aqueous solution of chloroacetic acid with a non-metal amino or hydroxy base;
   (b) reacting cis- or trans-1,2-diaminocyclohexane with a non-metal amino on hydroxy base;
   (c) treating the product from step (b) with a dilute solution of sodium hydroxide;
   (d) treating the resulting product of step (c) with acid and then
   (e) recovering the product formed.

2. The process of claim 1 wherein step (a) is conducted at a temperature not greater than 10° C.

3. The process of claim 2 wherein the reaction of step (b) is at a temperature 75°–80° C.

4. The process of claim 3, comprising the steps of:
(a) neutralizing chloroacetic acid in an aqueous medium with a non-metal amino or hydroxy base compound at a temperature of less than 10° C.;
(b) reacting said neutralized chloroacetic acid with 1,2-diaminohexane at a temperature of less than 80° C.;
(c) adding a non-metal amino or hydroxy base to complete neutralization so as to form an aqueous mixture;
(d) heating the aqueous mixture to a temperature of less than 100° C.;
(e) filtering the mixture from (d);
(f) treating the aqueous filtrate with hydrochloric acid until a precipitate forms;
(g) filtering the aqueous filtrate; and then
(h) recovering 1,2-diaminocyclohexanetetraacetic acid and optionally redissolving said 1,2-diaminocyclohexanetetraacetic acid in an aqueous solution and repeating step (c).

5. The process of claim 1 wherein the non-metal amino or hydroxy base is selected from the group consisting of sodium hydroxide, tetramethyl ammonium hydroxide, tetraethylammonium hydroxide, monoethanolamine, isopropylamine, diethanolamine, 2-amino-1-propanol, 2-amino-2-ethoxy propanol and mixtures thereof.

6. The process of claim 1 wherein the non-metal amino or hydroxy base in step (a) is different from that used in step (c).

7. The process of claim 1 wherein the non-metal amino at hydroxy base in step (a) is tetramethylammonium hydroxide and in step (b) ammonium hydroxide.

8. The process of claim 1 wherein sodium hydroxide is used as hydroxy base in steps (a) and (c).

9. The process of claim 3 wherein the non-metal amino or hydroxy base is selected from the group consisting of sodium hydroxide, tetramethyl ammonium hydroxide, tetraethylammonium hydroxide, monoethanolamine, isopropylamine, diethanolamine, 2-amino-1-propanol, 2-amino-2-ethoxy propanol and mixtures thereof.

10. The process of claim 3 wherein the non-metal amino or hydroxy base in step (a) is different from that used in step (c).

11. The process of claim 3 wherein the non-metal amino or hydroxy base in step (a) is tetramethylammonium hydroxide and in step (b) ammonium hydroxide.

12. The process of claim 3 wherein sodium hydroxide is used as hydroxy base in steps (a) and (c).

13. A process for preparing cis- or trans-1,2-diaminocyclohexane-N,N,N',N'-tetraacetic acid which comprises the steps of
(a) neutralizing chloroacetic acid in an aqueous medium with a non-metal amino or hydroxy base compound at a temperature of less than 10° C.;
(b) reacting said neutralized chloroacetic acid with 1,2-diaminohexane at a temperature of less than 80° C.;
(c) adding a non-metal amino or hydroxy base to complete neutralization so as to form an aqueous mixture;
(d) heating the aqueous mixture to a temperature of less than 100° C.;
(e) filtering the mixture from (d);
(f) treating the aqueous filtrate with hydrochloric acid until a precipitate forms;
(g) filtering the aqueous filtrate; and then
(h) recovering 1,2-diaminocyclohexanetetraacetic acid and optionally redissolving said 1,2-diaminocyclohexanetetraacetic acid in an aqueous solution and repeating steps (c) to (g),
wherein sodium hydroxide is used as hydroxy base in steps (a) and (c).

* * * * *